(12) United States Patent
Liu et al.

(10) Patent No.: US 9,044,519 B2
(45) Date of Patent: Jun. 2, 2015

(54) RADIOTRACER PRECURSOR FOR IMAGING OF HYPOXIC TISSUE, RADIOTRACER, AND METHOD FOR PREPARING THE SAME

(71) Applicant: ATOMIC ENERGY COUNCIL—INSTITUTE OF NUCLEAR ENERGY RESEARCH, Taoyuan County (TW)

(72) Inventors: Show-Wen Liu, Taoyuan County (TW); Yu Chang, Taoyuan County (TW); Cheng-Fang Hsu, Taoyuan County (TW); Tsung-Hsien Chiang, Taoyuan County (TW); Sheng-Lun Lin, Taoyuan County (TW); Chih-Yuan Lin, Taoyuan County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 74 days.

(21) Appl. No.: 13/920,364

(22) Filed: Jun. 18, 2013

(65) Prior Publication Data
US 2014/0371434 A1    Dec. 18, 2014

(51) Int. Cl.
*C07F 13/00*  (2006.01)
*A61K 51/04*  (2006.01)

(52) U.S. Cl.
CPC ......... *A61K 51/0478* (2013.01); *A61K 51/0474* (2013.01)

(58) Field of Classification Search
None
See application file for complete search history.

(56) References Cited

PUBLICATIONS

Choi et al. (Korea Atomic Energy Res. Inst. 2010) http://www.iaea.org/inis/collection/NCLCollectionStore/_Public/45/092/45092948.pdf.*

* cited by examiner

*Primary Examiner* — Michael G Hartley
*Assistant Examiner* — Melissa Perreira
(74) *Attorney, Agent, or Firm* — Rosenberg, Klein & Lee

(57) ABSTRACT

A radiotracer precursor for imaging of hypoxic tissues, a radiotracer and a method for preparing the same are revealed. The radiotracer precursor, DANI, includes a nitroimidazole functional group with a feature of retention in hypoxic tissues and a bifunctional ligand able to complex with radioisotopes. Thus DANI can be used to produce radiotracers stayed in hypoxic tissues and the radiotracers are applied to medical imaging of malignant tumor with hypoxic layer.

12 Claims, 4 Drawing Sheets

DANI

RADIOTRACER PRECURSOR FOR IMAGING OF HYPOXIC TISSUE, RADIOTRACER, AND METHOD FOR PREPARING THE SAME

BACKGROUND OF THE INVENTION

1. Fields of the Invention

The present invention relates to a radiotracer precursor, especially to a radiotracer precursor containing an organic ligand, 6-(2-nitroimidazde)-hexyl-L-3,6-diaza-4,7-dioxo-8 [(triphenylmethyl)thio]-2-[((triphenylmethyl)thio)methyl] octanamide (DANI), a radiotracer and a method for preparing the same.

2. Descriptions of Related Art

A lot of diseases cause hypoxia. Tissues or organs are deprived of adequate oxygen supply. For example, people have serious diseases such as stroke, myocardial infarction, malignant tumor, etc., their tissues have decreased oxygen supplies (hypoxia). This is due to acute or temporarily reduction of regional blood flow at myocardial cells or insufficient oxygen supply to malignant cells. Hypoxia is unpredictable. Thus non-invasive techniques for detecting hypoxia at various regions such as heart, brain, and tumor have been developed vigorously.

All mammals require oxygen for tissue metabolism. Generally, oxygen with low concentration (about 3~5 torr) flows from capillaries to cells therearound for metabolism/reactions in cells. Yet tumor causes changes in oxygen balance inside tissues. In order to maintain cell activity, tumor cells need additional oxygen supply. In order to meet such requirement, tumors cells have a specific feature that is to induce blood vessel growth in tissues. However, the amount of oxygen the malignant cells need is always larger than that of the oxygen the blood vessels supply. When oxygen gas diffuses across the cell membrane of capillaries, it is quickly metabolized by cells on outer layers and unable to diffuse into inner layers of the tumor. Thus cells inside solid tumors with larger size are in hypoxia due to insufficient oxygen and blood supply and cell breakdown (necrosis) occurs gradually after long term oxygen depletion. Therefore tumors include a certain ratio of hypoxic or necrosis cells in accordance with volume and biological characters of tumors.

For diagnosis and follow-up of the malignant tumors, hypoxic tissues are of great potential to be used as media/targets being detected by radionuclide imaging techniques.

Nuclear medicine imaging involves applications of radioisotopes in medical imaging for patients. Radiopharmaceuticals are taken internally, for example, intravenously, orally or inhaledly. After a period of time, the radiopharmaceuticals are attracted to specific organs or tissues. Then medical imaging machines such as gamma cameras are used to detect distribution of the radiopharmaceuticals in organs or tissues. For example, crystal of sodium iodide in the camera scintillates in response to incident gamma radiation so as to form images After development or computer processing, the images showing physiological changes are used as a diagnostic tool by doctors.

For detecting tumors hypoxia in vivo by radionuclide imaging techniques, a suitable radiotracer is a key factor.

SUMMARY OF THE INVENTION

Therefore it is a primary object of the present invention to provide a radiotracer precursor that includes a nitroimidazole group with a feature of retention in hypoxic tissues and a bifunctional ligand able to complex with radioisotopes. Thus the radioisotopes can be carried to the hypoxic tissues and having a potential used for labeling.

It is another object of the present invention to provide a radiotracer precursor that uses a triphenylmethyl group for protecting a thiol group. Thus the precursor not only has stable chemical properties but also convenience in storage. Before use, the triphenylmethyl group is released directly during complex reaction and this is quite convenient for users.

It is a further object of the present invention to provide a method for preparing a radiotracer precursor with good preservation and convenience.

It is a further object of the present invention to provide a radiotracer that includes both organic functional group with a feature of retention in hypoxic tissues and stable detectable radioisotopes. Morphology of hypoxic tissues, especially the hypoxic layer of malignant tumor can be learned through distribution of radiotracers being detected by associated medical equipment. Thus doctors can have valuable and sufficient information to make a diagnosis.

In order to achieve the above objects, the present invention provides a radiotracer precursor for imaging of hypoxic tissues, a radiotracer and a method for preparing the same. A bifunctional ligand is joined with a nitroimidazole or a nitroimidazole derivative and then connected to a radioisotope for labeling by complex reaction so as to form a radiotracer for hypoxic tissues. The radiotracer for hypoxic tissues is not only used for diagnosis but also applied to follow-up after treatment. Thus the radiotracer is an essential tool in diagnosis and treatment of malignant tumors.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Please refer to following embodiments for details, features and effects of the present invention.

Figure 1:
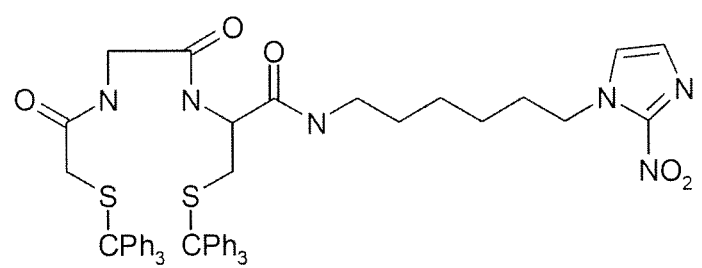
FIG. 1 shows a chemical structure of an embodiment of a radiotracer precursor, DANI, according to the present invention.

Refer to FIG. 1, a schematic drawing showing a chemical structure of a radiotracer precursor of the present invention is revealed. As shown in figure, DANI mentioned above includes a long alkyl group and a nitroimidazole so as to increase its lipid solubility. Moreover, nitroimidazole or its derivatives will have a series of redox-reactions after entering cells. If now the cell contains sufficient oxygen, nitroimidazole or its derivatives are exported out of the cell to be excreted. If the cell is in hypoxia, nitroimidazole or its derivatives are going to stay for a longer time. Due to retention of nitroimidazole in hypoxia tissue, nitroimidazole is labeled with radioisotopes to form hypoxia imaging agents with excellent performance.

Besides nitroimidazole, the radiotracer precursor also includes a bifunctional ligand that binds to radioactive isotopes in a five-coordinated manner to form a substance with stable pyramid structure. The substance is used as a radiotracer.

As mentioned above, the radiotracer precursor of the present invention includes nitroimidazole with a feature of retention in hypoxic tissues. In malignant tumor, cancer cells grow rapidly so that most of tumor has hypoxia. After being labeled with radioisotopes, the radiotracer produced can stay in malignant tumor, used as the imaging tracer.

Moreover, a thiol group of DANI is protected by $CPh_3$ so that the chemical properties are stable and the storage time is extended.

Figure 2:
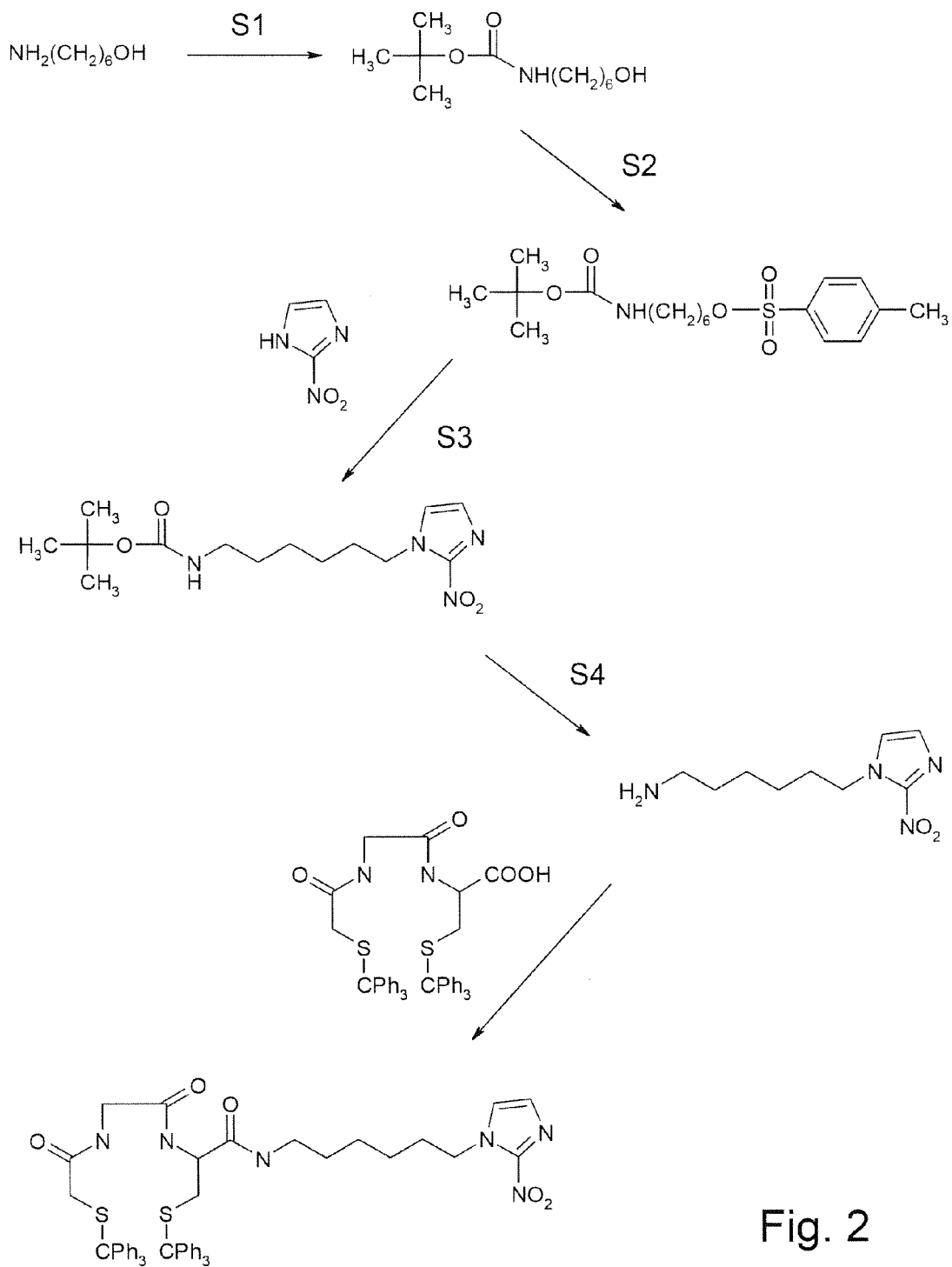
FIG. 2 is a schematic diagram showing the synthesis of DANI according to the present invention.

Refer to FIG. 2, a method for preparing a radiotracer precursor of the present invention is disclosed. The method includes following steps:

Step S1: Take 6-amino-1-hexanol to react with tert-butyl carbonate for amino group protection and get tert-butyl 6-hydroxycarbamate.

Step S2: Use tert-butyl 6-hydroxycarbamate and P-toluenesulfonyl chloride to perform a substitution reaction in pyridine solution and produce tert-butyl 6-toluenesulfonyl hexylcarbamate.

Step S3: Take tert-butyl 6-toluenesulfonyl hexylcarbamate and 2-nitroimidazole to carry out substitution reaction in dimethylformamide (DMF) solution and get tert-butyl 6-(2-nitroimidazole)-hexylcarbamate.

Step S4: Hydrogenize tert-butyl 6-(2-nitroimidazole)-hexylcarbamate to get 6-(2-nitroimidazole)-hexylamine. Then take 6-(2-nitroimidazole)-hexylamine and L-3,6-diaza-4,7-dioxo-8-[(triphenylmethyl)thio]-2-[(((triphenylmethyl)thio)methyl]octanoic acid to carry out amidation and get DANI.

In the step S1, the amino group protection reaction is performed in anhydrous dichloromethane ($CH_2Cl_2$). The reaction temperature is room temperature and the reaction time is 24 hours. As to the substitution in pyridine solution of Step S2, the reaction temperature is room temperature and the reaction time is 1 hour.

In the substitution reaction of step S3, Caesium carbonate ($Cs_2CO_3$) is used as a reactant together with 2-nitroimidazole to react in anhydrous dimethylformamide (DMF). The reaction temperature is 65 degrees Celsius and the reaction time is 2 hours. The amidation in the Step S4 uses 1,3-dicyclohexyl-carbodiimide (DCC) and N-hydroxysuccinimide (NHS) as reactants, reacted in trichloromethane solution. The reaction temperature is room temperature and the reaction time is 2.5 hours.

Figure 3:
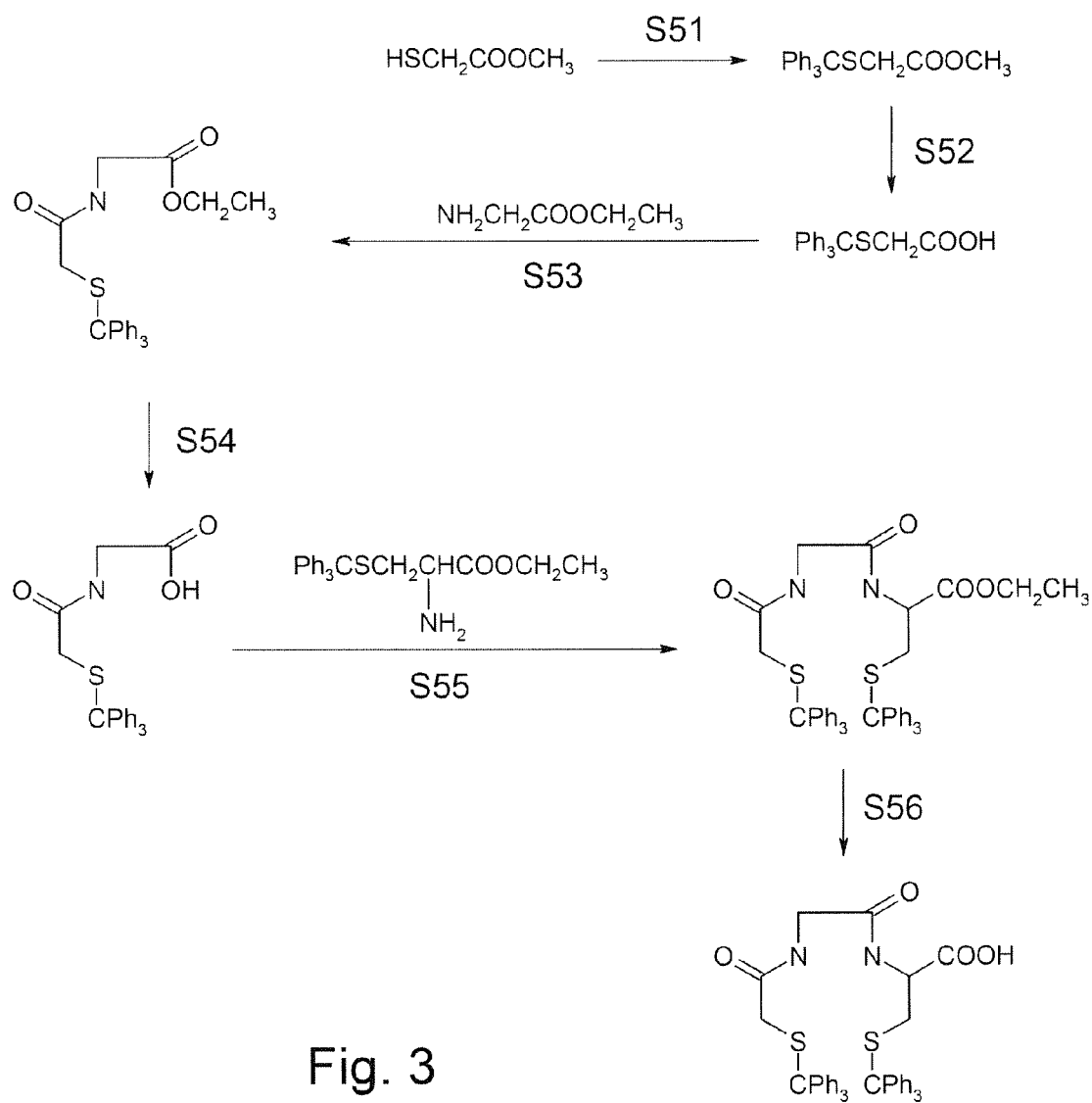
FIG. 3 is a schematic diagram showing the synthesis of a compound used for preparing DANI according to the present invention.

Refer to FIG. 3, a method for preparing L-3,6-diaza-4,7-dioxo-8-[(triphenylmethyl)thio]-2-[(((triphenylmethyl)thio)methyl]octanoic acid used in the step S4 includes following steps:

Step S51: Use a triphenylmethyl group to protect a thiol group of thioglycolic acid methyl ester and get triphenylmethyl thioglycolic acid methyl ester.

Step S52: Hydrolyze triphenylmethyl thioglycolic acid methyl ester in alkaline methanol solution to produce triphenylmethyl thioglycolic acid;

Step S53: Use triphenylmethyl thioglycolic acid and glycine ethyl ester to perform amidation and get 3-aza-4-oxo-5-[(triphenylmethyl)thio]-pentanoic acid ethyl ester.

Step S54: Hydrolyze 3-aza-4-oxo-5-[(triphenylmethyl)thio]-pentanoic acid ethyl ester in alkaline methanol solution to produce 3-aza-4-oxo-5-[(triphenylmethyl)thio]-pentanoic acid.

Step S55: Take 3-aza-4-oxo-5-[(triphenylmethyl)thio]-pentanoic acid and L-triphenylmethyl cysteine ethyl ester to carry out amidation and get L-3,6-diaza-4,7-dioxo-8-[(triphenylmethyl)-thio]-2-[(((triphenyl-methyl)thio)methyl]-octanoic acid ethyl ester.

Step S56: Hydrolyze L-3,6-diaza-4,7-dioxo-8-[(triphenylmethyl)-thio]-2-[(((triphenyl-methyl)thio)methyl]-octanoic acid ethyl ester to get L-3,6-Diaza-4,7-dioxo-8-[(triphenylmethyl)-thio]-2-[(((triphenyl-methyl)thio)methyl]-octanoic acid.

In the step S51, the catalyst is boron trifluoride ethyl ether complex while protecting thiol group by triphenylmethyl group. The solvent is trichloromethane (chloroform). The reaction temperature is room temperature and the reaction time is 24 hours.

The hydrolysis reaction in steps S52, S54, S56, etc. uses potassium hydroxide or sodium methoxide as a catalyst, being carried out in methanol solution.

In the step S53 and step S55, similar to the method of the step S4, DCC and NHS are used as reactants to react at room temperature for 24 hours. The amidation of the step S53 is carried out in trichloromethane solution while amidation of the step S55 is in Tetrahydrofuran (THF) solution.

Figure 4:
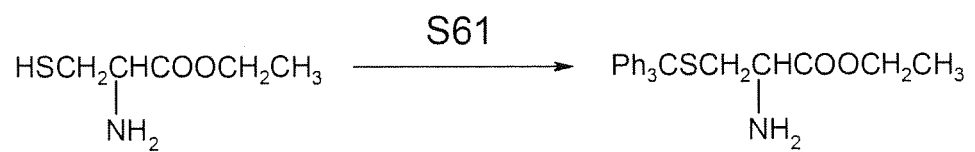
FIG. 4 is a schematic diagram showing the synthesis of a compound used for preparing DANI according to the present invention.

A method for preparing L-triphenylmethyl cysteine ethyl ester in the step S55 is using a triphenylmethyl group to protect a thiol group of L-cysteine methyl ester so as to get L-triphenylmethyl cysteine ethyl ester whose chemical structure is shown in the step S61 revealed in FIG. 4. In this step, boron trifluoride-diethyl etherate complex is used as a catalyst and the solvent is trichloromethane. The reaction temperature is 75 degrees Celsius and the reaction time is 4 hours.

According to the above steps, organic ligand DANI is prepared. The 2-nitroimidazole of DANI stays in hypoxic tissues such as the hypoxic layer of malignant tumor generated due to rapid growth of tumor cells. Thus the DANI has more advantages while being used as a radiotracer. The bifunctional ligand contained in DANI can also complex with radioisotopes so as to be detected by associated medical equipment.

Figure 5:
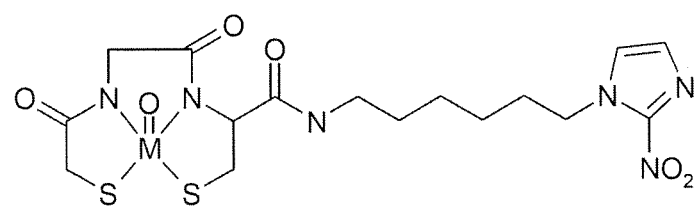
FIG. 5 shows a chemical structure of an embodiment of a radiotracer according to the present invention.

Refer to FIG. 5, a radiotracer containing the DANI organic ligand for imaging of hypoxia tissues is revealed. The difference between the radiotracer and the radiotracer precursor is in that DANI in the radiotracer has already connected with a radioisotope M. The triphenylmethyl group for protection is automatically released during complex reaction and there is no need to remove the protection group in advance. M is selected from one of the most common radioisotopes used in radionuclide imaging such as technetium-99m ($^{99m}Tc$), Rhenium-188 ($^{188}Re$) and Indium-115 ($^{115}In$), etc. After entering living bodies, the radiotracer stays in hypoxic tissues such as malignant tumor due to the 2-nitroimidazole group of the organic ligand DANI. Thus through PET (positron emission tomography) or SPET (single photon emission tomography) that detects distribution of radioisotopes ($^{99m}Tc$, $^{188}Re$, $^{115}In$, etc.), the malignant tumor can be imaged and observed clearly. Thus an accurate diagnosis is made and healthcare quality is improved significantly.

The followings are embodiments for preparing DANI.

Synthesis of L-Triphenylmethyl cysteine ethyl ester

Take and dissolve 9.3 g (50.0 mmol) L-cysteine ethyl ester hydrochloride and 7.9 mL (57.1 mmol) triethylamine in 100 mL trichloromethane. Then the solution is heated to reflux, add 13.0 g (50.0 mmol) triphenylmethanol into the solution, slowly 17 mL (135.0 mmol) drop boron trifluoride ethyl ether complex into the solution and continue the reflux for 4 hours. After being cooled down, wash the organic phase with saturated sodium bicarbonate aqueous solution (3×100 mL). Then organic phase is concentrated by vacuum concentration after being dried by anhydrous sodium sulfate. Use liquid chromatography (SiO$_2$, chloroform:ethyl acetate=4:1) for isolation and purification of L-Triphenylmethyl cysteine ethyl ester (14.0 g, 72%).

Synthesis of Triphenylmethyl thioglycolic acid methyl ester

Dissolve 5.0 mL (55.0 mmol) methyl thioglycolate and 14.3 g (55.0 mmol) triphenylmethanol in 80 mL trichloromethane. Then slowly drop 6.9 mL (55.0 mmol) boron trifluoride ethyl ether complex into the solution and stir the solution at room temperature. Use thin layer chromatography (TLC)(chloroform:hexane=1:1) to follow the reaction. After starting material disappeared completely, wash the reaction solution with water (2×100 mL). The organic phase is dried by anhydrous sodium sulfate and then the solvent is removed by vacuum evaporation to get 18.6 g (97.5%) Triphenylmethyl thioglycolic acid methyl ester.

Synthesis of Triphenylmethyl thioglycolic acid

Take and put 18.6 g (53.5 mmol) Triphenylmethyl thioglycolic acid methyl ester in 300 mL 10% potassium hydroxide in methanol solution and stir the solution at room temperature until triphenylmethyl thioglycolic acid being dissolved completely. After being concentrated by vacuum concentration, dissolve residue with 100 mL 50% methanol aqueous solution and drop concentrated hydrochloric acid into the solution until the pH value of the solution is 6. Use trichloromethane solution to extract (3×100 mL). Then after the organic phase being dried by anhydrous sodium sulfate, the solvent is removed by vacuum evaporation to get 17.9 g, (~100%) Triphenylmethyl thioglycolic acid.

Synthesis of 3-Aza-4-oxo-5-[(triphenylmethyl)thio]-pentanoic acid ethyl ester Dissolve 10.1 g (30.2 mmol) triphenylmethyl thioglycolic acid, 4.2 g (30.2 mmol) glycine ethyl ester hydrochloride, 10.4 mL (75.4 mmol) triethylamine, 9.3 g (45.3 mmol) 1,3-dicyclohexylcarbodiimide and 5.2 g (45.3 mmol) N-hydroxysuccinimide in 100 mL trichloromethane. Stir the solution overnight at room temperature and filter the solution. Wash the filtrate with water (1×100 mL). After being dried by anhydrous sodium sulfate, the organic phase is concentrated by vacuum concentration. Then use 100 mL acetonitrile to dissolve the residue and concentrate the acetonitrile solution. Use liquid chromatography (SiO$_2$, chloroform:hexane=1:1) for isolation and purification to get 9.6 g (75.5%) 3-Aza-4-oxo-5-[(triphenylmethyl)thio]pentanoic acid ethyl ester.

Synthesis of 3-Aza-4-oxo-5-[(triphenylmethyl)thio]-pentanoic acid

Take and dissolve 2.8 g (6.8 mmol) 3-Aza-4-oxo-5-[(triphenylmethyl)thio]pentanoic acid ethyl ester in 80 mL 10% potassium hydroxide in methanol and stir the solution overnight at room temperature. Then the solution is concentrated by vacuum concentration at room temperature, add 50 mL THF solution for dissolution, and drop concentrated hydrochloric acid into the solution until the pH of the solution is 6. After being concentrated, use methanol to dissolve residue. Next the methanol is removed by vacuum evaporation to get 1.5 g (60%) 3-Aza-4-oxo-5-[(triphenylmethyl)thio]pentanoic acid.

Synthesis of L-3,6-Diaza-4,7-dioxo-8-[(triphenylmethyl)-thio]-2-[((triphenyl-methyl)thio)-methyl]Octanoic Acid Ethyl Ester Take 1.2 g (2.9 mmol) L-Triphenylmethyl cysteine ethyl ester, 1.2 g (2.9 mmol) 3-Aza-4-oxo-5-[(triphenyl-methyl)thio]pentanoic acid, 0.9 g (4.4 mmol) 1,3-dicyclohexylcarbodiimide, 0.4 g (3.5 mmol) N-hydroxy-succinimide and dissolve them in 30 mL THF solution. Stir the solution overnight at room temperature, filter the solution and concentrate the filtrate by vacuum concentration. Use 30 mL acetonitrile to extract residue. After the acetonitrile solution being concentrated, use liquid chromatography (SiO$_2$, ethyl acetate:hexane=1:1) for isolation and purification to get 1.1 g (48%) L-3,6-Diaza-4,7-dioxo-8-[(triphenylmethyl)thio]-2-[((triphenyl-methyl)thio)methyl]octanoic acid ethyl ester.

Synthesis of L-3,6-Diaza-4,7-dioxo-8-[(triphenylmethyl)thio]-2-[((triphenyl-methyl)-thio)methyl]Octanoic Acid Take and put 1.1 g (1.4 mmol) L-3,6-Diaza-4,7-dioxo-8-[(triphenylmethyl)thio]-2-[((triphenyl-methyl)thio)methyl]octanoic acid ethyl ester into 30 mL 10% potassium hydroxide in methanol and stir the solution at room temperature for 3 hours. Then concentrate the solution by vacuum concentration at room temperature, add 30 mL THF solution to dissolve the residue, and drop concentrated hydrochloric acid into the solution until the pH of the solution is 6. Concentrate the solution by vacuum concentration again and extract the residue by 30 mL methanol. After being concentrated, the organic phase is isolated and purified by liquid chromatography (SiO$_2$, chloroform:methanol=9:1) to get 0.16 g (15.6%) L-3,6-Diaza-4,7-dioxo-8-[(triphenylmethyl)thio]-2-[((triphenyl-methyl)thio)-methyl]octanoic acid.

Synthesis of tert-butyl 6-hydroxycarbamate

Dissolve 5.05 g (43.1 mmol) 6-aminohexanol in 50 mL anhydrous dichloromethane. Add 12.3 mL (51.7 mmol) di-tert-butyl dicarbonate into the solution and stir the mixture overnight at room temperature. Wash with 100 mL Hexane. Take the part not dissolved in hexane and wash the part with 100 mL water. Get the organic phase layer and dehydrate the layer with Na2SO4. After being concentrated by vacuum concentration, a final product 9.06 g (97%) tert-butyl 6-hydroxycarbamate is obtained.

Synthesis of tert-butyl 6-toluenesulfonyl-hexylcarbamate

Dissolve 4.56 g (21.0 mmol) tert-butyl 6-hydroxycarbamate in 25 mL anhydrous pyride. Then slowly add 4.00 g (21.0 mmol) P-toluenesulfonyl chloride into the solution in an ice bath and stir the mixture at room temperature for 1 hour. Next add 25 mL water and concentrated hydrochloric acid for adjusting the pH value of the mixture to less than 7. Use 100 mL dichloromethane to extract twice. Take the organic layer, wash with 2N hydrochloric acid aqueous solution. Take the organic layer, add with anhydrous sodium sulfate for dehydration, and remove the solvent by vacuum evaporation. Use liquid chromatography (SiO2, EA:CHC13=1:2) for isolation and purification to get the product 4.82 g (62%) tert-butyl 6-toluenesulfonylhexylcarbamate.

Synthesis of tert-butyl 6-(2-Nitroimidazole)Hexylcarbamate

Take 1.64 g (4.42 mmol) tert-butyl 6-toluenesulfonylhexylcarbamate, 0.5 g (4.42 mmol) 2-nitroimidazole, and 1.44 g (4.42 mmol) $Cs_2CO_3$, add with 20 mL anhydrous DMF. Heat the mixture to 65° C. and stir the mixture for 2 hours. Then vacuum heat to 50° C. for evaporation and add chloroform for dissolution. Take the dissolved part and concentrate the dissolved part by vacuum concentration. Use liquid chromatography (EA:CHC13=1:4) for isolation and purification of the product tert-butyl 6-(2-nitroimidazole)-hexylcarbamate (0.68 g, 47%).

Synthesis of DANI

Take 0.24 g (0.71 mmol) 6-(2-nitroimidazole)-hexylamine obtained by hydrogenation of tert-butyl 6-(2-nitroimidazole) hexylcarbamate, 0.12 g (1.04 mmol) N-hydroxysuccinimide, 0.22 g (1.07 mmol) 1,3-dicyclohexylcarbodiimide, and 0.59 g (0.71 mmol) L-3,6-Diaza-4,7-dioxo-8-[(triphenylmethyl) thio]-2-[((triphenylmethyl)thio)methyl]octanoic acid, add with 100 mL chloroform and stir the mixture at room temperature for 2.5 hours. After being concentrated by vacuum concentration, add with acetone for dissolution. Then perform vacuum filtration, get the filtrate and concentrate the filtrate. Use liquid chromatography ($SiO_2$, $CHCl_3$: $CH_3OH$=100:10) for isolation and purification of the product DANI (0.48 g, 65%).

The DANI prepared according to the above steps is with good preservation. Before use, the DANI complexes with a radioisotope to form a radiotracer that is able to stay in hypoxic tissues through action of the functional group of DANI. At the same time, DANI makes the radioisotope precisely reach the hypoxic tissues inside living bodies to be used as an imaging tracer. Thus the radiotracer precursor for hypoxic tissues, the radiotracer and the method for preparing the same according to the present invention are of high practical value.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for preparing a radiotracer precursor comprising the steps of:
    using 6-amino-1-hexanol and tert-butyl carbonate to carry out amino group protection and get tert-butyl 6-hydroxycarbamate;
    using tert-butyl 6-hydroxycarbamate and P-toluenesulfonyl chloride to perform a substitution reaction in pyridine solution and produce tert-butyl 6-toluenesulfonyl hexylcarbamate;
    taking tert-butyl 6-toluenesulfonyl hexylcarbamate and 2-nitroimidazole to perform substitution reaction in dimethylformamide (DMF) solution and get tert-butyl 6-(2-nitroimidazole)hexylcarbamate; and
    hydrogenizing tert-butyl 6-(2-nitroimidazole) -hexylcarbamate to get 6-(2-nitroimidazole)hexylamine and 6-(2-nitroimidazole)hexylamine further reacting with L-3,6-diaza-4,7-dioxo-8-[(triphenylmethyl) -thio]-2-[((triphenylmethyl)thio)methyl]octanoic acid to carry out amidation and get (6-(2-nitroimidazde)hexyl-L-3,6-diaza-4,7-dioxo -8[(triphenylmethyl)thio]-2-[((triphenylmethyl)thio)m ethyl]octanamide (DANI).

2. The method claimed in claim 1, wherein a method for preparing L-3,6-diaza-4,7-dioxo-8-[(triphenylmethyl) -thio]-2-[((triphenylmethyl)thio)methyl]octanoic acid includes the steps of:
    using a triphenylmethyl group to protect a thiol group of thioglycolic acid methyl ester and get triphenylmethyl thioglycolic acid methyl ester;
    hydrolyzing triphenylmethyl thioglycolic acid methyl ester in alkaline methanol solution to produce triphenylmethyl thioglycolic acid;
    using triphenylmethyl thioglycolic acid and glycine ethyl ester to perform amidation and get 3-aza-4-oxo-5-[(triphenylmethyl)thio]-pentanoic acid ethyl ester;
    hydrolyzing 3-aza-4-oxo-5-[(triphenylmethyl) -thio]-pentanoic acid ethyl ester in alkaline methanol solution to produce 3-aza-4-oxo-5-[(triphenylmethyl)thio]-pentanoic acid;
    taking 3-aza-4-oxo-5-[(triphenylmethyl)thio]-pentanoic acid and L-triphenylmethyl cysteine ethyl ester to carry out amidation and get L-3,6-diaza-4,7-dioxo-8-[(triphenylmethyl)-thio]-2-[((triphenyl-methyl)thio)methyl]-octanoic acid ethyl ester; and
    hydrolyzing L-3,6-diaza-4,7-dioxo-8-[(triphenylmethyl) thio]-2-[((triphenyl-methyl) -thio)methyl]-octanoic acid ethyl ester to get L-3,6-Diaza-4,7-dioxo-8-[(triphenylmethyl)thio]-2-[((triphenyl-methyl)thio)methyl] octanoic acid.

3. The method as claimed in claim 2, wherein a method for preparing L-triphenylmethyl cysteine ethyl ester is using a triphenylmethyl group to protect a thiol group of L-cysteine methyl ester so as to get L-triphenylmethyl cysteine ethyl ester.

4. The method as claimed in claim 2, wherein in the step of using a triphenylmethyl group to protect a thiol group, boron trifluoride ethyl ether complex is used as a catalyst and the solvent is trichloromethane; reaction temperature is room temperature and reaction time is 24 hours.

5. The method as claimed in claim 3, wherein in the step of using a triphenylmethyl group to protect a thiol group, boron trifluoride-diethyl etherate complex is used as a catalyst and the solvent is trichloromethane; reaction temperature is 75 degrees Celsius and reaction time is 4 hours.

6. The method as claimed in claim 2, wherein in the steps of hydrolyzing, potassium hydroxide or sodium methoxide is used as a catalyst.

7. The method as claimed in claim 2, wherein in the step of using triphenylmethyl thioglycolic acid and glycine ethyl ester to perform amidation, 1,3-dicyclohexylcarbodiimide (DCC) and N-hydroxysuccinimide (NHS) are used as reactants, reacted in trichloromethane solution; reaction temperature is room temperature and reaction time is 24 hours.

8. The method as claimed in claim 2, wherein in the step of taking 3-aza-4-oxo-5-[(triphenylmethyl)thio]-pentanoic acid and L-triphenylmethyl cysteine ethyl ester to carry out amidation, 1,3-dicyclohexylcarbodiimide (DCC) and N-hydroxysuccinimide (NHS) are used as reactants, reacted in tetrahydrofuran solution; reaction temperature is room temperature and reaction time is 24 hours.

9. The method as claimed in claim 1, wherein the amino group protection is performed in anhydrous dichloromethane; reaction temperature is room temperature and reaction time is 24 hours.

10. The method as claimed in claim 1, wherein in the step of performing the substitution in pyridine solution, reaction temperature is room temperature and reaction time is 1 hour.

11. The method as claimed in claim 1, wherein in the step of performing the substitution reaction in DMF solution, Caesium carbonate ($Cs_2CO_3$) is used as a reactant; reaction temperature is 65 degrees Celsius and reaction time is 2 hours.

12. The method as claimed in claim 1, wherein the amidation uses 1,3-dicyclohexylcarbodiimide (DCC) and N-hydroxysuccinimide (NHS) as reactants, reacted in trichloromethane solution; the reaction temperature is room temperature and reaction time is 2.5 hours.

\* \* \* \* \*